(12) United States Patent
Wechter

(10) Patent No.: US 11,071,868 B2
(45) Date of Patent: *Jul. 27, 2021

(54) USER INTERFACE FOR CUSTOM PATTERNED ELECTRICAL STIMULATION

(71) Applicant: Boston Scientific Neuromodulation Corporation, Valencia, CA (US)

(72) Inventor: David Ernest Wechter, Austin, TX (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 43 days.

This patent is subject to a terminal disclaimer.

(21) Appl. No.: 16/410,975

(22) Filed: May 13, 2019

(65) Prior Publication Data

US 2019/0262622 A1 Aug. 29, 2019

Related U.S. Application Data

(63) Continuation of application No. 15/180,980, filed on Jun. 13, 2016, now Pat. No. 10,335,601.
(Continued)

(51) Int. Cl.
*A61N 1/372* (2006.01)
*A61N 1/05* (2006.01)
(Continued)

(52) U.S. Cl.
CPC ............ *A61N 1/37247* (2013.01); *A61B 5/24* (2021.01); *A61N 1/0556* (2013.01);
(Continued)

(58) Field of Classification Search
CPC ................................................ A61N 1/37247
See application file for complete search history.

(56) References Cited

U.S. PATENT DOCUMENTS

| 4,255,790 A | 3/1981 | Hondeghem |
| 4,931,858 A | 6/1990 | Honjo |

(Continued)

FOREIGN PATENT DOCUMENTS

| AU | 2015318142 B2 | 6/2018 |
| AU | 2015343483 B2 | 6/2018 |

(Continued)

OTHER PUBLICATIONS

"U.S. Appl. No. 14/853,589, Final Office Action dated Jan. 18, 2017", 12 pgs.

(Continued)

*Primary Examiner* — George R Evanisko
(74) *Attorney, Agent, or Firm* — Schwegman Lundberg & Woessner, P.A.

(57) ABSTRACT

A neurostimulation system includes a programming control circuit and a user interface. The programming control circuit may be configured to generate a plurality of stimulation parameters controlling delivery of neurostimulation pulses according to one or more neurostimulation programs each specifying a pattern of the neurostimulation pulses. The user interface includes a display screen, a user input device, and a neurostimulation program circuit. The neurostimulation program circuit may be configured to allow for construction of one or more pulse trains (PTs) and one or more train groupings (TGs) of the one or more neurostimulation programs, and to allow for scheduling of delivery of the one or more neurostimulation programs, using the display screen and the user input device. Each PT includes one or more pulse blocks each including a plurality of pulses of the neurostimulation pulses. Each TG includes one or more PTs.

20 Claims, 7 Drawing Sheets

Related U.S. Application Data

(60) Provisional application No. 62/198,957, filed on Jul. 30, 2015.

(51) Int. Cl.

| | | |
|---|---|---|
| *A61N 1/36* | (2006.01) | |
| *G16H 40/63* | (2018.01) | |
| *A61B 5/24* | (2021.01) | |
| *G06F 3/0483* | (2013.01) | |
| *G06F 3/0484* | (2013.01) | |
| *G06F 3/0488* | (2013.01) | |
| *A61B 5/00* | (2006.01) | |

(52) U.S. Cl.
CPC ...... *A61N 1/36053* (2013.01); *A61N 1/36114* (2013.01); *A61N 1/37264* (2013.01); *G06F 3/0483* (2013.01); *G06F 3/0488* (2013.01); *G06F 3/04842* (2013.01); *G16H 40/63* (2018.01); *A61B 5/4035* (2013.01); *A61B 5/7475* (2013.01)

(56) References Cited

U.S. PATENT DOCUMENTS

| | | | |
|---|---|---|---|
| 4,935,674 A | 6/1990 | Rodriguez-cavazos | |
| 5,300,096 A | 4/1994 | Hall et al. | |
| 5,360,437 A | 11/1994 | Thompson | |
| 5,369,224 A | 11/1994 | Miyata | |
| 5,381,524 A | 1/1995 | Lewis et al. | |
| 5,576,979 A | 11/1996 | Lewis et al. | |
| 5,713,937 A | 2/1998 | Nappholz et al. | |
| 5,724,985 A | 3/1998 | Snell et al. | |
| 5,725,560 A | 3/1998 | Brink | |
| 6,266,566 B1 | 7/2001 | Nichols et al. | |
| 6,516,227 B1 | 2/2003 | Meadows et al. | |
| 6,675,046 B2 | 1/2004 | Holsheimer | |
| 6,895,280 B2 | 5/2005 | Meadows et al. | |
| 6,993,384 B2 | 1/2006 | Bradley et al. | |
| 7,003,349 B1 | 2/2006 | Andersson et al. | |
| 7,228,179 B2 | 6/2007 | Campen et al. | |
| 7,317,948 B1 | 1/2008 | King et al. | |
| 7,333,856 B1 | 2/2008 | Er et al. | |
| 7,333,857 B2 | 2/2008 | Campbell | |
| 7,539,538 B2 | 5/2009 | Parramon et al. | |
| 7,650,184 B2 | 1/2010 | Walter | |
| 7,664,849 B1 | 2/2010 | Chandler et al. | |
| 7,783,353 B2 | 8/2010 | Libbus et al. | |
| 7,826,901 B2 | 11/2010 | Lee et al. | |
| 7,979,119 B2 | 7/2011 | Kothandaraman et al. | |
| 7,979,133 B2 | 7/2011 | Feler et al. | |
| 7,983,762 B2 | 7/2011 | Gliner et al. | |
| 8,019,439 B2 | 9/2011 | Kuzma et al. | |
| 8,224,453 B2 | 7/2012 | De Ridder | |
| 8,255,057 B2 | 8/2012 | Fang et al. | |
| 8,285,389 B2 | 10/2012 | Libbus et al. | |
| 8,340,775 B1 * | 12/2012 | Cullen .................. | G16H 40/63 607/59 |
| 8,355,797 B2 | 1/2013 | Caparso et al. | |
| 8,455,716 B2 | 6/2013 | Huang et al. | |
| 8,504,147 B2 | 8/2013 | Deem et al. | |
| 8,560,080 B2 | 10/2013 | Goetz et al. | |
| 8,615,300 B2 | 12/2013 | Feler et al. | |
| 8,649,874 B2 | 2/2014 | Alataris et al. | |
| 8,670,831 B2 | 3/2014 | Wacnik et al. | |
| 8,676,329 B2 | 3/2014 | Wacnik et al. | |
| 8,676,331 B2 | 3/2014 | Parker | |
| 8,692,843 B2 | 4/2014 | Bloemer | |
| 8,694,113 B2 | 4/2014 | Smoorenburg | |
| 8,731,675 B2 | 5/2014 | Ranu et al. | |
| 8,751,009 B2 | 6/2014 | Wacnik | |
| 8,798,755 B2 | 8/2014 | Grill et al. | |
| 8,874,211 B2 | 10/2014 | Libbus et al. | |
| 9,265,948 B2 | 2/2016 | Libbus et al. | |
| 9,737,717 B2 | 8/2017 | Moffitt et al. | |
| 9,802,052 B2 | 10/2017 | Marnfeldt | |
| 10,335,601 B2 * | 7/2019 | Wechter .................. | A61B 5/24 |
| 10,449,360 B2 | 10/2019 | Moffitt et al. | |
| 10,456,586 B2 | 10/2019 | Wechter et al. | |
| 2002/0077669 A1 | 6/2002 | Lindh et al. | |
| 2002/0077859 A1 | 6/2002 | Stahmann et al. | |
| 2002/0115939 A1 | 8/2002 | Mulligan et al. | |
| 2003/0139781 A1 | 7/2003 | Bradley et al. | |
| 2003/0176899 A1 | 9/2003 | Samuelsson et al. | |
| 2004/0111131 A1 | 6/2004 | Hu et al. | |
| 2005/0177206 A1 | 8/2005 | North et al. | |
| 2006/0149337 A1 | 7/2006 | John | |
| 2006/0241720 A1 | 10/2006 | Woods et al. | |
| 2007/0150036 A1 | 6/2007 | Anderson | |
| 2007/0299663 A1 | 12/2007 | Fado et al. | |
| 2008/0158175 A1 | 7/2008 | Hotelling et al. | |
| 2008/0163097 A1 | 7/2008 | Goetz et al. | |
| 2008/0188909 A1 | 8/2008 | Bradley | |
| 2009/0024189 A1 | 1/2009 | Lee et al. | |
| 2009/0043359 A1 | 2/2009 | Smoorenburg | |
| 2009/0198305 A1 | 8/2009 | Naroditsky et al. | |
| 2009/0204173 A1 | 8/2009 | Fang et al. | |
| 2010/0010390 A1 | 1/2010 | Skelton et al. | |
| 2010/0010566 A1 | 1/2010 | Thacker et al. | |
| 2010/0010646 A1 | 1/2010 | Drew et al. | |
| 2010/0121409 A1 | 5/2010 | Kothandaraman et al. | |
| 2010/0274312 A1 | 10/2010 | Alataris et al. | |
| 2010/0274314 A1 | 10/2010 | Alataris et al. | |
| 2010/0274315 A1 | 10/2010 | Alataris et al. | |
| 2010/0274317 A1 | 10/2010 | Parker et al. | |
| 2010/0274318 A1 | 10/2010 | Walker et al. | |
| 2010/0274326 A1 | 10/2010 | Chitre et al. | |
| 2010/0331916 A1 | 12/2010 | Parramon et al. | |
| 2011/0046697 A1 | 2/2011 | Gerber et al. | |
| 2011/0054570 A1 | 3/2011 | Lane | |
| 2011/0093051 A1 | 4/2011 | Davis et al. | |
| 2011/0208012 A1 | 8/2011 | Gerber et al. | |
| 2012/0059446 A1 | 3/2012 | Wallace et al. | |
| 2012/0083709 A1 | 4/2012 | Parker et al. | |
| 2012/0109006 A1 | 5/2012 | James et al. | |
| 2012/0197336 A1 | 8/2012 | Su | |
| 2012/0253422 A1 | 10/2012 | Thacker et al. | |
| 2012/0265267 A1 | 10/2012 | Blum et al. | |
| 2012/0265279 A1 | 10/2012 | Zhu et al. | |
| 2012/0283797 A1 | 11/2012 | De Ridder | |
| 2012/0290041 A1 | 11/2012 | Kim et al. | |
| 2012/0296396 A1 | 11/2012 | Moffitt et al. | |
| 2012/0302912 A1 | 11/2012 | Moffitt et al. | |
| 2013/0041283 A1 | 2/2013 | Wichner | |
| 2013/0053926 A1 | 2/2013 | Hincapie Ordonez et al. | |
| 2013/0060304 A1 | 2/2013 | Wichner | |
| 2013/0066411 A1 | 3/2013 | Thacker et al. | |
| 2013/0116752 A1 | 5/2013 | Parker et al. | |
| 2013/0131760 A1 | 5/2013 | Rao et al. | |
| 2013/0226261 A1 | 8/2013 | Sparks et al. | |
| 2013/0268021 A1 | 10/2013 | Moffitt | |
| 2013/0268026 A1 * | 10/2013 | Rao .................. | A61N 1/37247 607/59 |
| 2013/0296975 A1 | 11/2013 | Lee et al. | |
| 2013/0304152 A1 | 11/2013 | Bradley et al. | |
| 2014/0005743 A1 | 1/2014 | Giuffrida et al. | |
| 2014/0052033 A1 | 2/2014 | Lawlis et al. | |
| 2014/0067016 A1 | 3/2014 | Kaula et al. | |
| 2014/0074179 A1 | 3/2014 | Heldman et al. | |
| 2014/0074180 A1 | 3/2014 | Heldman et al. | |
| 2014/0074190 A1 | 3/2014 | Griffith | |
| 2014/0081349 A1 | 3/2014 | Lee et al. | |
| 2014/0081354 A1 | 3/2014 | Davis et al. | |
| 2014/0172045 A1 | 6/2014 | Yip et al. | |
| 2014/0257425 A1 | 9/2014 | Arcot-Krishnamurthy et al. | |
| 2014/0257428 A1 | 9/2014 | Zhu | |
| 2014/0276181 A1 | 9/2014 | Sun et al. | |
| 2014/0277267 A1 | 9/2014 | Vansickle et al. | |
| 2015/0012057 A1 | 1/2015 | Carlson et al. | |
| 2015/0051666 A1 | 2/2015 | Roy et al. | |
| 2015/0165209 A1 | 6/2015 | Grandhe et al. | |
| 2015/0224307 A1 | 8/2015 | Bolea | |
| 2015/0238762 A1 | 8/2015 | Pal et al. | |
| 2015/0297893 A1 | 10/2015 | Kokones et al. | |

(56) References Cited

U.S. PATENT DOCUMENTS

| | | | |
|---|---|---|---|
| 2015/0328461 | A1 | 11/2015 | Charlesworth et al. |
| 2015/0328462 | A1 | 11/2015 | Griffith |
| 2015/0328467 | A1 | 11/2015 | Demers et al. |
| 2015/0343242 | A1 | 12/2015 | Tyler et al. |
| 2016/0027293 | A1 | 1/2016 | Esteller et al. |
| 2016/0074662 | A1 | 3/2016 | Moffitt et al. |
| 2016/0074663 | A1 | 3/2016 | De Ridder |
| 2016/0121126 | A1 | 5/2016 | Marnfeldt |
| 2016/0279429 | A1 | 9/2016 | Hershey et al. |
| 2017/0050033 | A1 | 2/2017 | Wechter |
| 2017/0106197 | A1 | 4/2017 | Wechter et al. |
| 2017/0333718 | A1 | 11/2017 | Moffitt et al. |
| 2019/0381328 | A1 | 12/2019 | Wechter et al. |
| 2020/0016409 | A1 | 1/2020 | Moffitt et al. |

FOREIGN PATENT DOCUMENTS

| | | |
|---|---|---|
| AU | 2016297965 B2 | 4/2019 |
| AU | 2018202528 B2 | 3/2020 |
| CN | 201333263 Y | 10/2009 |
| CN | 102413870 A | 4/2012 |
| CN | 102474544 A | 5/2012 |
| CN | 202933390 U | 5/2013 |
| CN | 103717260 A | 4/2014 |
| CN | 103889504 A | 6/2014 |
| CN | 203777499 U | 8/2014 |
| CN | 104548342 A | 4/2015 |
| CN | 106687173 A | 5/2017 |
| CN | 107073269 A | 8/2017 |
| CN | 107921255 A | 4/2018 |
| CN | 108463266 A | 8/2018 |
| CN | 107073269 B | 5/2020 |
| EP | 3194021 B1 | 10/2018 |
| EP | 3328481 B1 | 5/2019 |
| EP | 3362139 B1 | 7/2020 |
| JP | 1057508 A | 3/1998 |
| JP | 20100534114 A | 11/2010 |
| JP | 2013533092 A | 8/2013 |
| JP | 2014518722 A | 8/2014 |
| JP | 2017527429 A | 9/2017 |
| JP | 2017533072 A | 11/2017 |
| JP | 6452936 B2 | 12/2018 |
| WO | WO-03051175 A2 | 6/2003 |
| WO | WO-3051175 A2 | 6/2003 |
| WO | WO-2006029257 A2 | 3/2006 |
| WO | WO-2006135791 A2 | 12/2006 |
| WO | WO-2009067610 A1 | 5/2009 |
| WO | WO-2014159880 A1 | 10/2014 |
| WO | WO-2016004230 A1 | 1/2016 |
| WO | WO-2016044169 A1 | 3/2016 |
| WO | WO-2016073271 A1 | 5/2016 |
| WO | WO-2016154375 A1 | 9/2016 |
| WO | WO-2016172239 A1 | 10/2016 |
| WO | WO-2017019191 A1 | 2/2017 |
| WO | WO-2017066187 A1 | 4/2017 |

OTHER PUBLICATIONS

"U.S. Appl. No. 14/853,589, Non Final Office Action dated Aug. 17, 2016", 14 pgs.
"U.S. Appl. No. 14/853,589, Notice of Allowance dated Apr. 17, 2017", 5 pgs.
"U.S. Appl. No. 14/853,589, Response filed Mar. 14, 2017 to Final Office Action dated Jan. 18, 2017", 12 pgs.
"U.S. Appl. No. 14/853,589, Response filed Nov. 17, 2016 to Non Final Office Action dated Aug. 17, 2016", 12 pgs.
"U.S. Appl. No. 14/926,725, Corrected Notice of Allowance dated Jul. 17, 2017", 2 pgs.
"U.S. Appl. No. 14/926,725, Non-Final Office Action dated Mar. 3, 2017", 13 pgs.
"U.S. Appl. No. 14/926,725, Notice of Allowability dated Jul. 28, 2017", 2 pgs.
"U.S. Appl. No. 14/926,725, Notice of Allowance dated Jun. 27, 2017", 8 pgs.
"U.S. Appl. No. 14/926,725, Response filed May 25, 2017 to Non Final Office Action dated Mar. 3, 2017", 12 pgs.
"U.S. Appl. No. 15/079,340, Advisory Action dated Jun. 21, 2018", 3 pgs.
"U.S. Appl. No. 15/079,340, Final Office Action dated Apr. 4, 2018", 12 pgs.
"U.S. Appl. No. 15/079,340, Non Final Office Action dated Oct. 3, 2017", 10 pgs.
"U.S. Appl. No. 15/079,340, Response filed Jun. 4, 2018 to Final Office Action dated Apr. 4, 2018", 10 pgs.
"U.S. Appl. No. 15/079,340, Response filed Dec. 20, 2017 to Non Final Office Action dated Oct. 3, 2017", 10 pgs.
"U.S. Appl. No. 15/180,980, Advisory Action dated May 24, 2018", 5 pgs.
"U.S. Appl. No. 15/180,980, Examiner Interview Summary dated Apr. 30, 18", 3 pgs.
"U.S. Appl. No. 15/180,980, Examiner Interview Summary dated Oct. 10, 2018", 3 pgs.
"U.S. Appl. No. 15/180,980, Final Office Action dated Mar. 1, 2018", 10 pgs.
"U.S. Appl. No. 15/180,980, Non Final Office Action dated Jul. 19, 2018", 10 pgs.
"U.S. Appl. No. 15/180,980, Non Final Office Action dated Sep. 21, 2017", 9 pgs.
"U.S. Appl. No. 15/180,980, Notice of Allowance dated Feb. 14, 2019", 9 pgs.
"U.S. Appl. No. 15/180,980, Repsonse filed Dec. 20, 2017 to Non Final Office Action dated Sep. 21, 2017", 15 pgs.
"U.S. Appl. No. 15/180,980, Response filed Jul. 2, 2018 to Advisory Action dated May 24, 2018", 11 pgs.
"U.S. Appl. No. 15/180,980, Response filed Oct. 8, 2018 to Non Final Office Action dated Jul. 19, 2018", 12 pgs.
"Australian Application Serial No. 2015318142, First Examiners Report dated Sep. 15, 2017", 3 pgs.
"Australian Application Serial No. 2015318142, Response filed Feb. 8, 2018 to First Examiners Report dated Sep. 15, 2017", 15 pgs.
"Australian Application Serial No. 2015343483, First Examiners Report dated Sep. 19, 2017", 3 pgs.
"Australian Application Serial No, 2015343483, Response filed Feb. 8, 2018 to First Examiners Report dated Sep. 19, 2017", 17 pgs.
"Australian Application Serial No. 2016297965, First Examination Report dated Jun. 19, 2018", 3 pgs.
"European Application Serial No. 15767069.6, Response filed Nov. 23, 2017 to Communication Pursuant to Rules 161 and 162 EPC dated May 19, 2017", 12 pgs.
"European Application Serial No. 15791183.5, Response filed Feb. 6, 2018 to Communication Pursuant to Rules 161 & 162 EPC dated Jul. 27, 2017", 12 pgs.
"International Application Serial No. PCT/US15/58017, International Search Report dated Apr. 6, 2016", 5 pgs.
"International Application Serial No. PCT/US15/58017, Written Opinion dated Apr. 6, 2016", 8 pgs.
"International Application Serial No. PCT/US2015/049993, International Preliminary Report on Patentability dated Mar. 30, 2017", 6 pgs.
"International Application Serial No. PCT/US2015/049993, International Search Report dated Jan. 14, 2016", 3 pgs.
"International Application Serial No. PCT/US2015/049993, Written Opinion dated Jan. 14, 2016", 4 pgs.
"International Application Serial No. PCT/US2015/058017, International Preliminary Report on Patentability dated May 18, 2017", 10 pgs.
"International Application Serial No. PCT/US2016/023888, International Preliminary Report on Patentability dated Oct. 5, 2017", 7 pgs.
"International Application Serial No. PCT/US2016/023888, International Search Report dated Jun. 6, 2016", 5 pgs.
"International Application Serial No. PCT/US2016/023888, Written Opinion dated Jun. 6, 2016", 5 pgs.

(56) References Cited

OTHER PUBLICATIONS

"International Application Serial No. PCT/US2016/037226, International Preliminary Report on Patentability dated Feb. 8, 2018", 7 pgs.
"International Application Serial No. PCT/US2016/037226, International Search Report dated Aug. 25, 2016", 4 pgs.
"International Application Serial No. PCT/US2016/037226, Written Opinion dated Aug. 25, 2016", 5 pgs.
"International Application Serial No. PCT/US2016/056426, International Preliminary Report on Patentability dated Apr. 26, 2018", 8 pgs.
"International Application Serial No. PCT/US2016/056426, International Search Report dated Jan. 26, 2017", 5 pgs.
"International Application Serial No. PCT/US2016/056426, Written Opinion dated Jan. 26, 2017", 6 pgs.
"U.S. Appl. No. 15/079,340, Advisory Action dated Apr. 8, 2019", 3 pgs.
"U.S. Appl. No. 15/079,340, Examiner Interview Summary dated Mar. 5, 2019", 3 pgs.
"U.S. Appl. No. 15/079,340, Examiner Interview Summary dated Jun. 17, 2019", 3 pgs.
"U.S. Appl. No. 15/079,340, Final Office Action dated Jan. 10, 2019", 13 pgs.
"U.S. Appl. No. 15/079,340, Non Final Office Action dated May 13, 2019", 13 pgs.
"U.S. Appl. No. 15/079,340, Non Final Office Action dated Jul. 27, 2018", 12 pgs.
"U.S. Appl. No. 15/079,340, Response filed Mar. 4, 2019 to Final Office Action dated Jan. 10, 2019", 12 pgs.
"U.S. Appl. No. 15/079,340, Response filed Oct. 29, 2018 to Non Final Office Action dated Jul. 27, 2018", 10 pgs.
"U.S. Appl. No. 15/079,340, Supplemental Amendment and Response dated Apr. 10, 2019", 14 pgs.
"U.S. Appl. No. 15/290,776, Examiner Interview Summary dated Oct. 12, 2018", 3 pgs.
"U.S. Appl. No. 15/290,776, Final Office Action dated Jan. 31, 2019", 24 pgs.
"U.S. Appl. No. 15/290,776, Non Final Office Action dated Jul. 12, 2018", 18 pgs.
"U.S. Appl. No. 15/290,776, Notice of Allowance dated Apr. 24, 2019", 8 pgs.
"U.S. Appl. No. 15/290,776, Response filed Oct. 8, 2018 to Non Final Office Action dated Jul. 12, 2018", 11 pgs.
"U.S. Appl. No. 15/290,776, Response filed Mar. 19, 2019 to Final Office Action dated Jan. 31, 2019", 8 pgs.
"U.S. Appl. No. 15/670,328, Non Final Office Action dated Jan. 14, 2019", 10 pgs.
"U.S. Appl. No. 15/670,328, Non Final Office Action dated Apr. 24, 2019", 7 pgs.
"U.S. Appl. No. 15/670,328, Notice of Allowance dated Jun. 11, 2019", 6 pgs.
"U.S. Appl. No. 15/670,328, Response filed Apr. 9, 2019 to Non Final Office Action dated Jan. 14, 2019", 11 pgs.
"U.S. Appl. No. 15/670,328, Response filed May 23, 2019 to Non Final Office Action dated Apr. 24, 2019", 8 Pgs.
"Australian Application Serial No. 2016297965, Response filed Feb. 22, 2019 to First Examination Report dated Jun. 19, 2018", 13 pgs.
"Australian Application Serial No. 2018202528, First Examination Report dated Dec. 21, 2018", 3 pgs.
"Australian Application Serial No. 2018202528, Response filed Oct. 18, 2019 to First Examination Report dated Dec. 21, 2018", 14 pgs.
"Chinese Application Serial No. 201580048568.3, Office Action dated Mar. 28, 2019", w/ English Translation, 26 pgs.
"Chinese Application Serial No. 201580048568.3, Office Action dated Jul. 31, 2018", with English translation, 24 pgs.
"Chinese Application Serial No. 201680047457.5, Office Action dated Jul. 28, 2020", w/ English translation, 20 pgs.
"European Application Serial No. 16732137.1, Response filed Oct. 15, 2018 to Communication Pursuant to Rules 161 and 162 EPC dated Apr. 3, 2018", 10 pgs.
"European Application Serial No. 16784712.8, Response filed Dec. 14, 2018 to Communication Pursuant to Rules 161 and 162 dated Jun. 4, 2018", 15 pgs.
"European Application Serial No. 18201843.2, Extended European Search Report dated Jan. 2, 2019", 6 pgs.
"European Application Serial No. 18201843.2, Response filed Sep. 25, 2019 to Extended European Search Report dated Jan. 2, 2019", 10 pgs.
"Japanese Application Serial No. 2017-542797, Office Action dated May 21, 2018", with English Translation, 4 pgs.
Carlson, Dave, et al., "A Flexible Algorithm Framework for Closed-Loop Neuromodulation Research Systems", Annual International Conference of the IEEE EMBS, (Jul. 31, 2013), 6146-6150.
Moffitt, Michael A., et al., "Graphical User Interface for Programming Neurostimulation Pulse Patterns", U.S. Appl. No. 14/853,589, filed Sep. 14, 2015.
Rao, Prakash, et al., "Technique for Linking Electrodes Together During Programming of Neurostimulation System", U.S. Appl. No. 61/561,760, filed Nov. 18, 2011.
Vansickle, Dennis Allen, et al., "Neuromodulation System and Method for Transitioning Between Programming Modes", U.S. Appl. No. 14/214,752, filed Mar. 15, 2014, 159 pgs.
Vansickle, Dennis Allen, "Systems and Methods for Delivering Sub-Threshold Therapy to a Patient", U.S. Appl. No. 61/801,917, filed Mar. 15, 2013.

* cited by examiner

USER INTERFACE FOR CUSTOM PATTERNED ELECTRICAL STIMULATION

CLAIM OF PRIORITY

This application is a continuation of U.S. application Ser. No. 15/180,980, filed Jun. 13, 2016, which claims the benefit of priority under 35 U.S.C. § 119(e) of U.S. Provisional Patent Application Ser. No. 62/198,957, filed on Jul. 30, 2015, which is herein incorporated by reference in its entirety.

TECHNICAL FIELD

This document relates generally to medical devices and more particularly to a programming method and apparatus using a user interface that allows a user to customize various patterns of electrical stimulation pulses.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, the human nervous systems use neural signals having much more sophisticated patterns to communicate various types of information, including sensations of pain, pressure, temperature, etc. The nervous system may interpret an artificial stimulation with a simple pattern of stimuli as an unnatural phenomenon, and respond with an unintended and undesirable sensation and/or movement. For example, some neurostimulation therapies are known to cause paresthesia and/or vibration of non-targeted tissue or organ.

Recent research has shown that the efficacy and efficiency of certain neurostimulation therapies can be improved, and their side-effects can be reduced, by using patterns of neurostimulation pulses that emulate natural patterns of neural signals observed in the human body. While modern electronics can accommodate the need for generating such sophisticated pulse patterns, the capability of a neurostimulation system depends on its post-manufacturing programmability to a great extent. For example, a sophisticated pulse pattern may only benefit a patient when it is customized for that patient, and stimulation patterns predetermined at the time of manufacturing may substantially limit the potential for the customization. Such customization may be performed at least in part by a user such as a physician or other caregiver with the patient in a clinical setting.

SUMMARY

An example (e.g., "Example 1") of a neurostimulation system includes a programming control circuit and a user interface. The programming control circuit may be configured to generate a plurality of stimulation parameters controlling delivery of neurostimulation pulses according to one or more neurostimulation programs each specifying a pattern of the neurostimulation pulses. The user interface is coupled to the programming control circuit and includes a display screen, a user input device, and a neurostimulation program circuit coupled to the display screen and the user input device. The neurostimulation program circuit may include a program creation module configured to create building blocks for the one or more neurostimulation programs and a program scheduling module configured to schedule delivery of the one or more neurostimulation programs. The program creation module may include a pulse train (PT) construction module and a train grouping (TG) construction module. The PT construction module may be configured to allow for construction of one or more PTs using the display screen and the user input device. The one or more PTs each include one or more pulse blocks (PBs) each including a plurality of pulses of the neurostimulation pulses. The TG construction module may be configured to allow for construction of one or more TGs using the display screen and the user input device. The one or more TGs each include one or more PTs.

In Example 2, the subject matter of Example 1 may optionally be configured such that the display screen includes a touchscreen, and a portion of the user input device is integrated into the touchscreen.

In Example 3, the subject matter of any one or any combination of Examples 1 and 2 may optionally be configured such that the neurostimulation program circuit is configured to display a neurostimulation program area on the screen in response to a neurostimulation programming command and to receive user commands using the user input device. The user commands include a program creation command and a program scheduling command.

In Example 4, the subject matter of Example 3 may optionally be configured such that the neurostimulation program circuit is configured to display a program creation tab and a program scheduling tab on the screen, to receive the program creation command when the program creation tab is selected, and to receive the program scheduling command when the program scheduling tab is selected.

In Example 5, the subject matter of any one or any combination of Examples 3 and 4 may optionally be configured such that the program creation module is configured to display a PT construction area and a TG construction area on the screen in response to the program creation command.

In Example 6, the subject matter of Example 5 may optionally be configured such that the PT construction module is configured to display a PT of the one or more PTs on the PT construction area and allow definition of the plurality of pulses in each PB of the one or more PBs of the PT.

In Example 7, the subject matter of Example 6 may optionally be configured such that the TG construction module is configured to display a TG of the one or more TGs on the TG construction area and allow definition of the TG as a sequence of PTs each selected from the one or more PTs.

In Example 8, the subject matter of Example 7 may optionally be configured such that the TG construction module is configured to allow specification of a number of repetitions for the one or more PBs of each PT of the sequence of PTs.

In Example 9, the subject matter of any one or any combination of Examples 7 and 8 may optionally be configured such that the TG construction module is configured to allow specification of an order of the one or more PBs of each PT of the sequence of PTs.

In Example 10, the subject matter of any one or any combination of Examples 3 to 9 may optionally be configured such that the program scheduling module is configured to display a program scheduling area on the screen in response to the program scheduling command and to allow scheduling of each program of the one or more neurostimulation programs including time of delivery for each TG of the one or more TGs in the each program.

In Example 11, the subject matter of Example 10 may optionally be configured such that the program scheduling module is configured to allow specification of a frequency of delivery of the each program.

In Example 12, the subject matter of any one or any combination of Examples 10 and 11 may optionally be configured such that the program scheduling module is configured to allow scheduling on a plurality of programs of the one or more neurostimulation programs to be delivered simultaneously.

In Example 13, the subject matter of any one or any combination of Examples 1 to 12 may optionally be configured to further include a storage device including a PT library having one or more stored PTs, and the PT construction module is configured to allow use of the one or more stored PTs in the construction of the one or more PTs and to allow each newly constructed PT of the one or more PTs to be added to the one or more stored PTs in the PT library.

In Example 14, the subject matter of Example 13 may optionally be configured such that the storage device further comprises a TG library having one or more stored TGs, and the TG construction module is configured to allow use of the one or more stored TGs in the construction of the one or more TGs and to allow each newly constructed TG of the one or more TGs to be added to the one or more stored TGs in the TG library.

In Example 15, the subject matter of any one or any combination of Examples 13 and 14 may optionally be configured such that the storage device further comprises a program library having one or more scheduled programs, and the program scheduling module is configured to allow to schedule a new program by rescheduling a scheduled program of the one or more scheduled programs and to allow each newly scheduled program to be added to the one or more scheduled programs in the program library.

An example of a method (e.g., Example 16") for delivering neurostimulation pulses is also provided. The method includes displaying a neurostimulation program area on a user interface and generating a plurality of stimulation parameters controlling delivery of the neurostimulation pulses based on one or more neurostimulation programs each specifying a pattern of the neurostimulation pulses. The neurostimulation program area allows a user to create building blocks for the one or more neurostimulation programs and to schedule delivery of the one or more neurostimulation programs. The one or more building blocks include one or more pulse blocks (PBs) each including a plurality of pulses of the neurostimulation pulses, one or more pulse trains (PTs) each including one or more PBs, and one or more train groupings (TGs) each including one or more PTs.

In Example 17, the subject matter of Example 16 may optionally further include delivering the neurostimulation pulses using an implantable medical device.

In Example 18, the subject matter of Example 16 may optionally include receiving user commands from the user using the user interface, the user commands including a program creation command and a program scheduling command.

In Example 19, the subject matter of Example 18 may optionally include displaying a program creation tab and a program scheduling tab on the screen, receiving the program creation command when the program creation tab is selected, and receiving the program scheduling command when the program scheduling tab being selected.

In Example 20, the subject matter of Example 19 may optionally include displaying a PT construction area and a TG construction area on the screen in response to the program creation command, receiving from the user a selection of a PT from the one or more PTs, displaying the selected PT in the PT construction area, allowing the user to define the plurality of pulses in each PB of the one or more PBs of the selected PT, receiving from the user a selection of a TG from the one or more TGs, displaying the selected TG in the TG construction area, and allowing the user to define the TG as a sequence of PTs each selected from the one or more PTs.

In Example 21, the subject matter of Example 20 may optionally include receiving from the user a number of repetitions for the one or more PBs of each PT of the sequence of PTs.

In Example 22, the subject matter of Example 21 may optionally include receiving from the user an order of the one or more PBs of each PT of the sequence of PTs.

In Example 23, the subject matter of Example 19 may optionally include displaying a program scheduling area on the screen in response to the programming scheduling command, receiving from the user a selection of a program from the one or more neurostimulation programs, displaying the selected program in the program scheduling area, and allowing the user to schedule the selected program, including specifying time of delivery for each TG of the one or more TGs in the each program.

In Example 24, the subject matter of Example 23 may optionally include allowing the user to specify a frequency of delivery of the each program.

In Example 25, the subject matter of Example 23 may optionally include receiving from the user he user to schedule a plurality of neurostimulation programs of the one or more neurostimulation programs to be run simultaneously.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
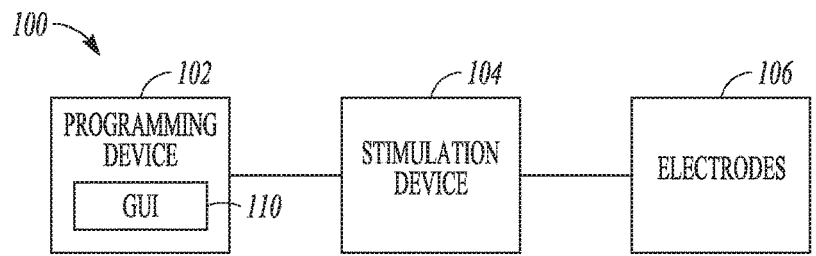
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a method and system for programming neurostimulation pulse patterns using a user interface, such as a graphical user interface (GUI). Advancements in neuroscience and neurostimulation research have led to a demand for using complex and/or individually optimized patterns of neurostimulation pulses for various types of therapies. The capability of a neurostimulation system in treating various types of disorders will be limited by the programmability of such patterns of neurostimulation pulses. In various embodiments, the present system allows for custom definition of a pattern of neurostimulation pulses, which includes custom definition of waveforms being the building blocks of the pattern. Such custom definition is achieved by using a user interface that makes it possible for the user to perform the custom definition of potentially very complex patterns of neurostimulation pulses by creating and editing graphical representations of relatively simple individual building blocks for each of the patterns. In various embodiments, the individually definable waveforms may include pulses, pulse blocks each including a burst of pulses, pulse trains each including a sequence of pulse blocks, train groups each including a sequence of pulse trains, and neurostimulation programs (also referred to as "programs" in this document) each including one or more train groups scheduled for delivery. In various embodiments, the present system provides for patterns of neurostimulation pulses not limited to waveforms predefined at the time of manufacturing, thereby accommodating need for customization of neurostimulation pulse patterns as well as need for new types of neurostimulation pulse patterns that may, for example, result from future research in neurostimulation. This may also facilitate design of a general-purpose neurostimulation device that can be configured by a user for delivering specific types of neurostimulation therapies by programming the device using the user interface.

In various embodiments, the present subject matter may be implemented using is a combination of hardware and software designed to provide users such as physicians of other caregivers with ability to create custom waveforms and patterns in an effort to increase therapeutic efficacy and/or patient satisfaction for neurostimulation therapies, including but not being limited to SCS and DBS therapies. While neurostimulation is specifically discussed as an example, the present subject matter may apply to any therapy that employs stimulation pulses of electrical or other form of energy.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In various embodiments, programming device 102 includes a user interface that allows the user to set and/or adjust values of the user-programmable parameters by creating and/or editing graphical representations of various waveforms. Such waveforms may include, for example, the waveform of a pattern of neurostimulation pulses to be delivered to the patient as well as individual waveforms that are used as building blocks of the pattern of neurostimulation pulses. Examples of such individual waveforms include pulses, pulse groups, and groups of pulse groups, as further discussed below. The user may also be allowed to define an electrode selection specific to each individually defined waveform. In the illustrated embodiment, the user interface includes a GUI 110. While a GUI is specifically discussed as an example of the user interface of the present system, any type of user interface accommodating various functions of the GUI as discussed in this document can be used as the user interface of the present system.

Figure 2:
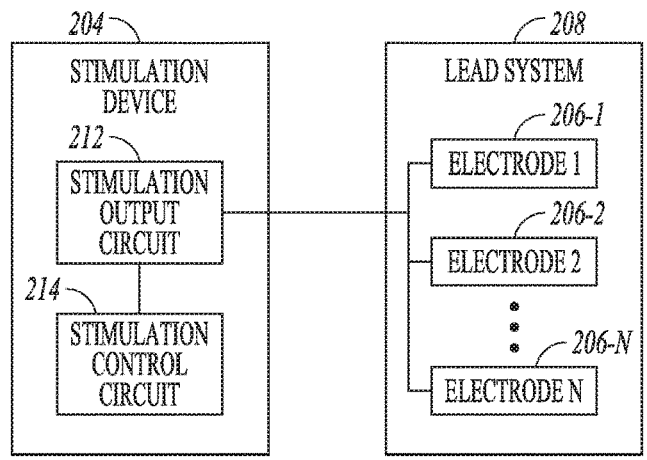
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an embodiment of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
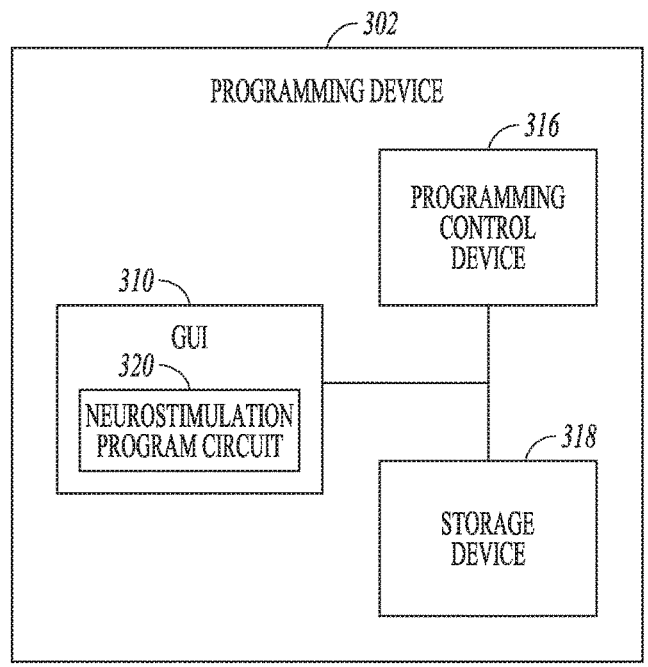
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a GUI 310. Storage device 318 stores a plurality of individually definable waveforms. Programming control circuit 316 generates the plurality of stimulation parameters that controls the delivery of the neurostimulation pulses according to the pattern of the neurostimulation pulses. GUI 310 represents an embodiment of GUI 110 and allows the user to define the pattern of the neurostimulation pulses using one or more waveforms selected from the plurality of individually definable waveforms.

In various embodiments, GUI 310 includes a neurostimulation program circuit 320 that creates neurostimulation programs and schedules delivery of the neurostimulation programs. In various embodiments, neurostimulation program circuit 320 allows the user to create each neurostimulation program using individually definable waveforms or building blocks such as pulses, pulse blocks each including a burst of pulses, pulse trains each including a sequence of pulse blocks, and train groupings each including a sequence of pulse trains. In various embodiments, neurostimulation program circuit 320 allows the user to schedule delivery of each neurostimulation program, such as by specifying delivery time for certain building blocks and a frequency at which the program is delivered. In various embodiments, neurostimulation program circuit 320 allows the user to create each building block or program using one or more waveforms stored in storage device 318 as templates. In various embodiments, neurostimulation program circuit 320 allows each newly created building block or program to be saved as additional waveforms stored in storage device 318.

In one embodiment, GUI 310 includes a touchscreen. In various embodiments, GUI 310 includes any type of presentation device, such as interactive or non-interactive screens, and any type of user input devices that allow the user to edit the waveforms or building blocks and schedule the programs, such as touchscreen, keyboard, keypad, touchpad, trackball, joystick, and mouse. In various embodiments, circuits of neurostimulation 100, including its various embodiments discussed in this document, may be implemented using a combination of hardware and software. For example, the circuit of GUI 100, stimulation control circuit 214, and programming control circuit 316, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
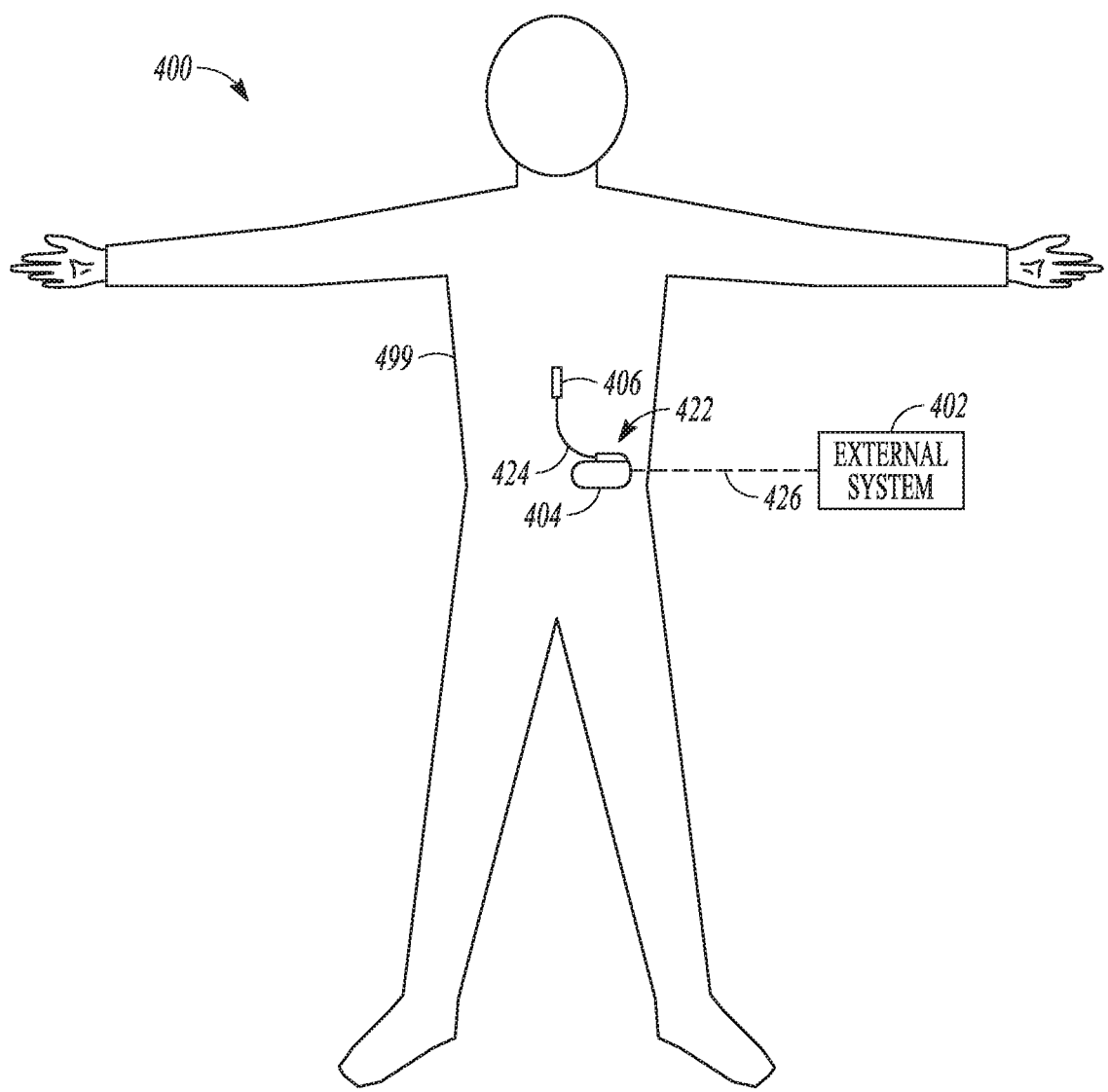
FIG. 4 illustrates an implantable neurostimulation system and portions of an environment in which the system may be used.

FIG. 4 illustrates an implantable neurostimulation system 400 and portions of an environment in which system 400 may be used. System 400 includes an implantable system 422, an external system 402, and a telemetry link 426 providing for wireless communication between implantable system 422 and external system 402. Implantable system 422 is illustrated in FIG. 4 as being implanted in the patient's body 499.

Implantable system 422 includes an implantable stimulator (also referred to as an implantable pulse generator, or IPG) 404, a lead system 424, and electrodes 406, which represent an embodiment of stimulation device 204, lead system 208, and electrodes 206, respectively. External system 402 represents an embodiment of programming device 302. In various embodiments, external system 402 includes one or more external (non-implantable) devices each allowing the user and/or the patient to communicate with implantable system 422. In some embodiments, external 402 includes a programming device intended for the user to initialize and adjust settings for implantable stimulator 404 and a remote control device intended for use by the patient. For example, the remote control device may allow the patient to turn implantable stimulator 404 on and off and/or adjust certain patient-programmable parameters of the plurality of stimulation parameters.

Figure 5:
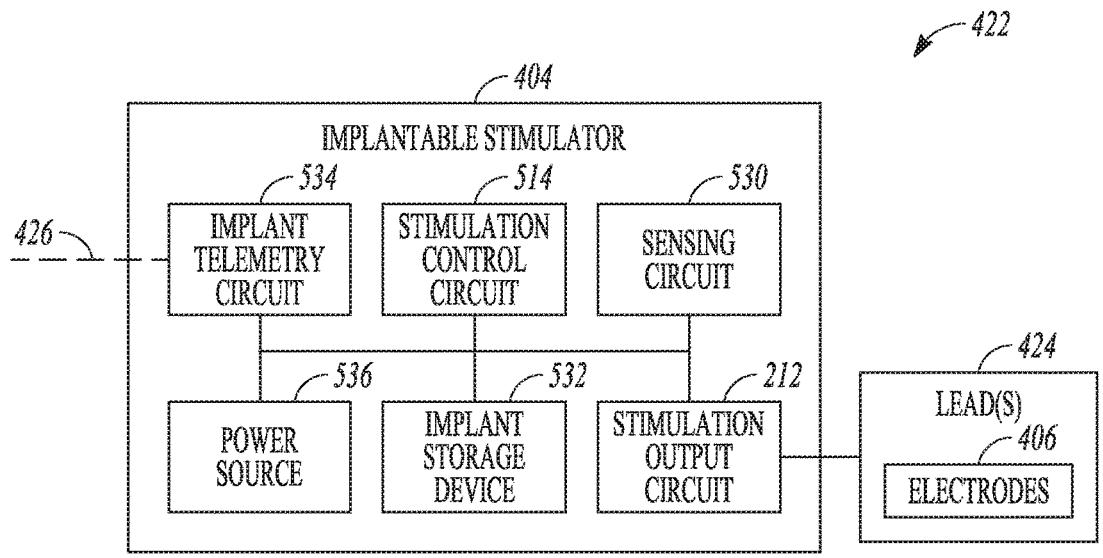
FIG. 5 illustrates an embodiment of an implantable stimulator and one or more leads of an implantable neurostimulation system, such as the implantable system of FIG. 4.

FIG. 5 illustrates an embodiment of implantable stimulator 404 and one or more leads 424 of an implantable neurostimulation system, such as implantable system 422. Implantable stimulator 404 may include a sensing circuit 530 that is optional and required only when the stimulator has a sensing capability, stimulation output circuit 212, a stimulation control circuit 514, an implant storage device 532, an implant telemetry circuit 534, and a power source 536. Sensing circuit 530, when included and needed, senses one or more physiological signals for purposes of patient monitoring and/or feedback control of the neurostimulation. Examples of the one or more physiological signals includes neural and other signals each indicative of a condition of the patient that is treated by the neurostimulation and/or a response of the patient to the delivery of the neurostimulation. Stimulation output circuit 212 is electrically connected to electrodes 406 through lead 424, and delivers each of the neurostimulation pulses through a set of electrodes selected from electrodes 406. Stimulation control circuit 514 represents an embodiment of stimulation control circuit 214 and controls the delivery of the neurostimulation pulses using the plurality of stimulation parameters specifying the pattern of the neurostimulation pulses. In one embodiment, stimulation control circuit 514 controls the delivery of the neurostimulation pulses using the one or more sensed physiological signals. Implant telemetry circuit 534 provides implantable stimulator 404 with wireless communication with another device such as a device of external system 402, including receiving values of the plurality of stimulation parameters from external system 402. Implant storage device 532 stores values of the plurality of stimulation parameters. Power source 536 provides implantable stimulator 404 with energy for its operation. In one embodiment, power source 536 includes a battery. In one embodiment, power source 536 includes a rechargeable battery and a battery charging circuit for charging the rechargeable battery. Implant telemetry circuit 534 may also function as a power receiver that receives power transmitted from external system 402 through an inductive couple.

In various embodiments, sensing circuit 530 (if included), stimulation output circuit 212, stimulation control circuit 514, implant telemetry circuit 534, implant storage device 532, and power source 536 are encapsulated in a hermetically sealed implantable housing. In various embodiments, lead(s) 424 are implanted such that electrodes 406 are places on and/or around one or more targets to which the neurostimulation pulses are to be delivered, while implantable stimulator 404 is subcutaneously implanted and connected to lead(s) 424 at the time of implantation.

Figure 6:
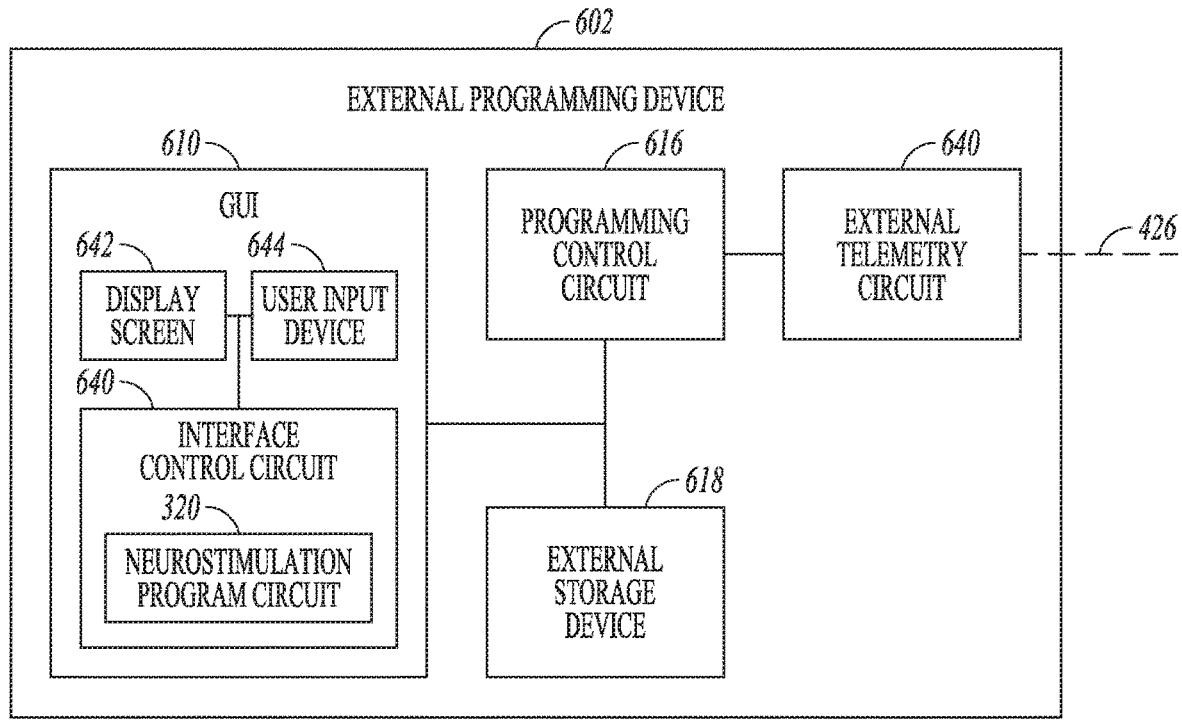
FIG. 6 illustrates an embodiment of an external programming device of an implantable neurostimulation system, such as the external system of FIG. 4.

FIG. 6 illustrates an embodiment of an external programmer 602 of an implantable neurostimulation system, such as external system 402. External programmer 602 represents an embodiment of programming device 302, and includes an external telemetry circuit 640, an external storage device 618, a programming control circuit 616, and a GUI 610.

External telemetry circuit 640 provides external programmer 602 with wireless communication with another device such as implantable stimulator 404 via telemetry link 426, including transmitting the plurality of stimulation parameters to implantable stimulator 404. In one embodiment, external telemetry circuit 640 also transmits power to implantable stimulator 404 through the inductive couple.

External storage device 618 stores a plurality of individually definable waveforms each selectable for use as a portion of the pattern of the neurostimulation pulses. In various embodiments, each waveform of the plurality of individually definable waveforms includes one or more pulses of the neurostimulation pulses, and may include one or more other waveforms of the plurality of individually definable waveforms. Examples of such waveforms include pulses, pulse blocks, pulse trains, and train groupings, and programs, as discussed below with reference to FIGS. 7 and 8. External storage device 618 also stores a plurality of individually definable fields. Each waveform of the plurality of individually definable waveforms is associated with one or more fields of the plurality of individually definable fields. Each field of the plurality of individually definable fields is defined by one or more electrodes of the plurality of electrodes through which a pulse of the neurostimulation pulses is delivered and a current distribution of the pulse over the one or more electrodes.

Programming control circuit 616 represents an embodiment of programming control circuit 316 and generates the plurality of stimulation parameters, which is to be transmitted to implantable stimulator 404, based on the pattern of the neurostimulation pulses. The pattern is defined using one or more waveforms selected from the plurality of individually definable waveforms stored in external storage device 618. In various embodiment, programming control circuit 616 checks values of the plurality of stimulation parameters against safety rules to limit these values within constraints of the safety rules. In one embodiment, the safety rules are heuristic rules.

GUI 610 represents an embodiment of user interface 310 and allows the user to define the pattern of neurostimulation pulses and perform various other monitoring and programming tasks. GUI 610 includes a display screen 642, a user input device 644, and an interface control circuit 640. Display screen 642 may include any type of interactive or non-interactive screens, and user input device 644 may include any type of user input devices that supports the various functions discussed in this document, such as touchscreen, keyboard, keypad, touchpad, trackball, joystick, and mouse. In one embodiment, GUI 610 includes an interactive screen that displays a graphical representation of a stimulation waveform and allows the user to adjust the waveform by graphically editing the waveform and/or various building blocks of the waveform. GUI 610 may also allow the user to perform any other functions discussed in this document where graphical editing is suitable as may be appreciated by those skilled in the art.

Interface control circuit 640 controls the operation of GUI 610 including responding to various inputs received by user input device 644 and defining the one or more stimulation waveforms. Interface control circuit 640 includes neurostimulation control circuit 320.

In various embodiments, external programming device 602 has operation modes including a composition mode and a real-time programming mode. Under the composition mode (also known as the pulse pattern composition mode), GUI 610 is activated, while programming control circuit 616 is inactivated. Programming control circuit 616 does not dynamically updates values of the plurality of stimulation parameters in response to any change in the one or more stimulation waveforms. Under the real-time programming mode, both GUI 610 and programming control circuit 616 are activated. Programming control circuit 616 dynamically updates values of the plurality of stimulation parameters in response to changes in the set of one or more stimulation waveforms, and transmits the plurality of stimulation parameters with the updated values to implantable stimulator 404.

Figure 7:
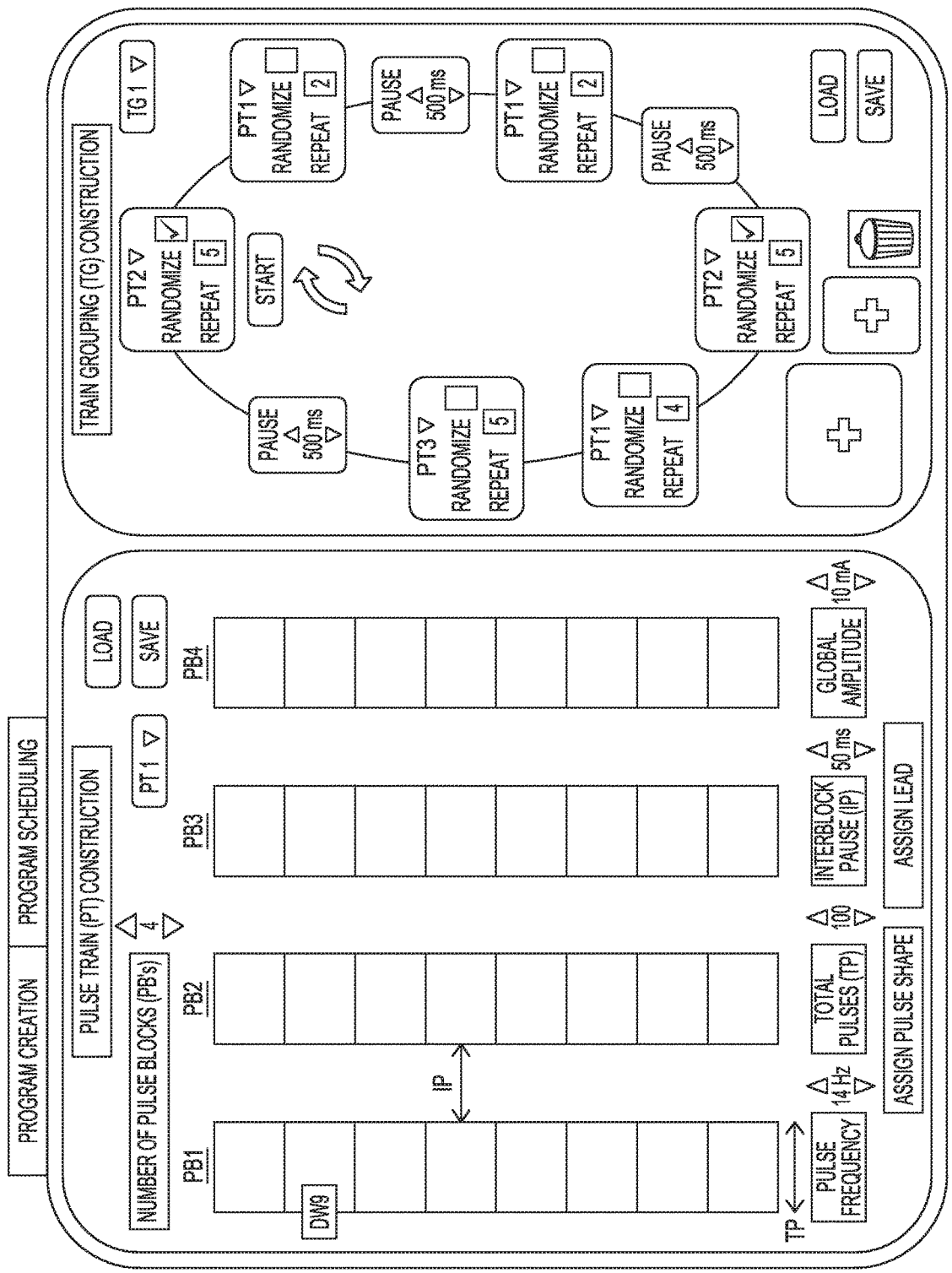
FIG. 7 is an illustration of an embodiment of a program creation area on a display screen of a graphical user interface (GUI).

FIG. 7 is an illustration of an embodiment of a program creation area on a display screen of a GUI, such as on display screen 642 of GUI 610. In the illustrated embodiment, the program creation area is displayed in response to a program creation tab being selected, and includes a pulse train (PT) construction area and a train grouping (TG) construction area.

In the illustrated embodiment, a neurostimulation program includes one or more TGs. Each TG includes one or more PTs. An inter-train pause may be introduced between adjacent PTs in a TG. Each PT includes one or more pulse blocks (PBs). Order of PBs in each PT may be programmable, such as selectable from a predetermined order and a randomized. Number of repetition of PBs in each PT may be programmable. Each PB includes a plurality of pulses. Programmable parameters associated with the PBs include pulse frequency, total pulses (TP), inter-block pause (IP), global amplitude, pulse shape, and lead (field) through which the pulses are delivered to the patient.

In the illustrated embodiment, the PT construction area includes a Load button and a Save button. The Load button allows for loading of a stored PT, such as from external storage device 618. The stored PT may be used as a template in creating a new PT. The Save button allows for saving a created PT, such as in external storage device 618. The TG construction area includes a Load button and a Save button. The Load button allows for loading of a stored TG, such as from external storage device 618. The stored TG may be used as a template in creating a new TG. The Save button allows for saving a created TG, such as in external storage device 618.

Figure 8:
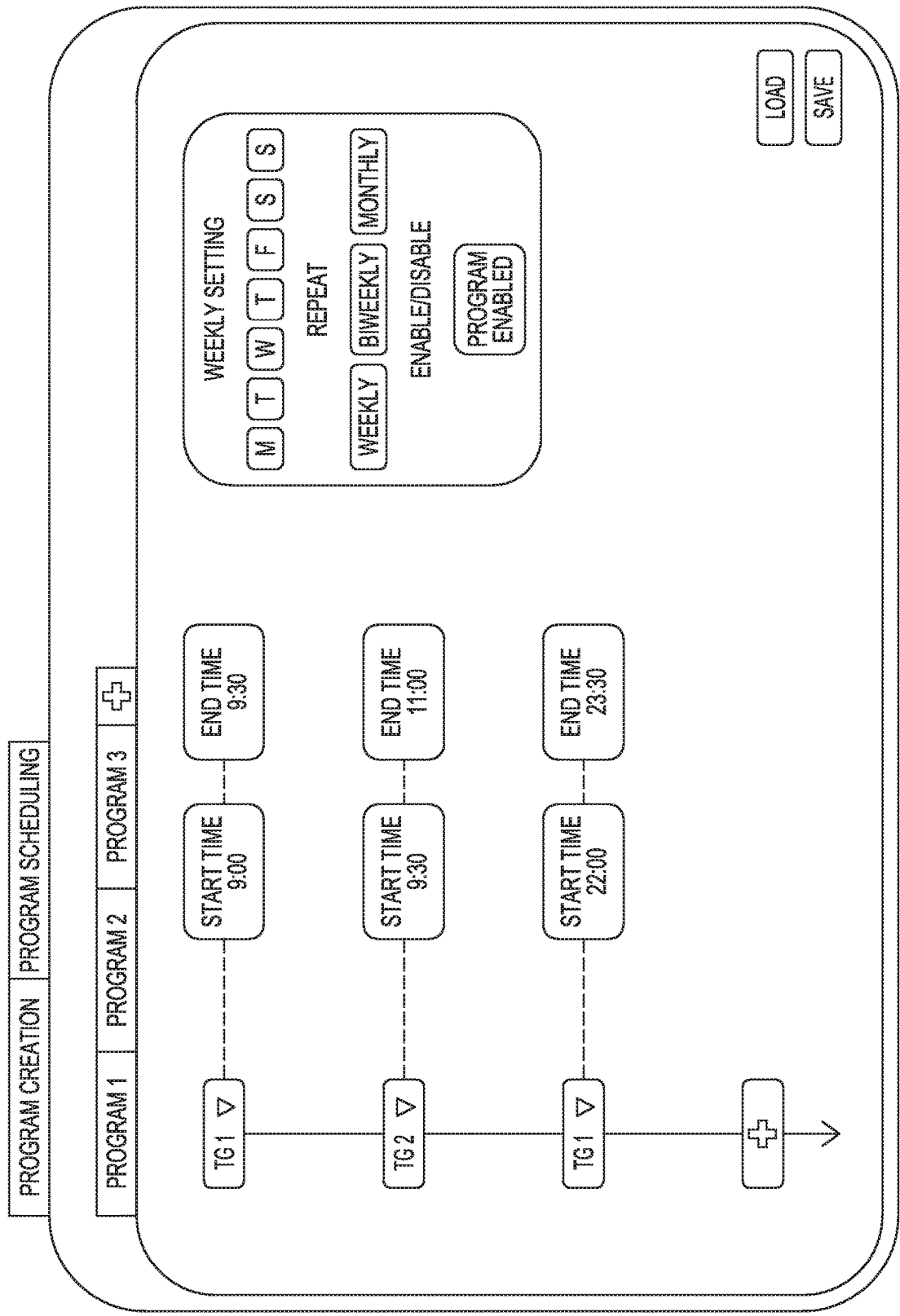
FIG. 8 is an illustration of an embodiment of a program scheduling area on a display screen of the GUI.

FIG. 8 is an illustration of an embodiment of a program scheduling area on a display screen of the GUI, such as on display screen 642 of GUI 610. In the illustrated embodiment, the program scheduling area is displayed in response to a program scheduling tab being selected, and allows for scheduling delivery of one or more neurostimulation programs.

In the illustrated embodiment, scheduling delivery for each program includes specifying time of delivery for each TG in a program. This includes specifying time of a day for starting the delivery of a TG and time of the day for ending the delivery of the TG. In an alternative embodiment, a predetermined duration for the delivery of the TG may be specified, in place of the time of the day for ending the delivery of the TG.

In the illustrated embodiment, scheduling delivery for each program further includes specifying a frequency of delivery of the program. This includes selecting weekly settings (days of a week on which the program is to be delivered), repetition (the program to be delivered weekly, biweekly, or monthly), and whether the program is enabled (selected for delivery). Multiple programs may be enabled simultaneously for simultaneous or concurrent delivery.

In the illustrated embodiment, the program scheduling area includes a Load button and a Save button. The Load button allows for loading of a stored scheduled program, such as from external storage device 618. The stored scheduled program may be used as a template in scheduling a new program. The Save button allows for saving a scheduled program, such as in external storage device 618.

Figure 9:
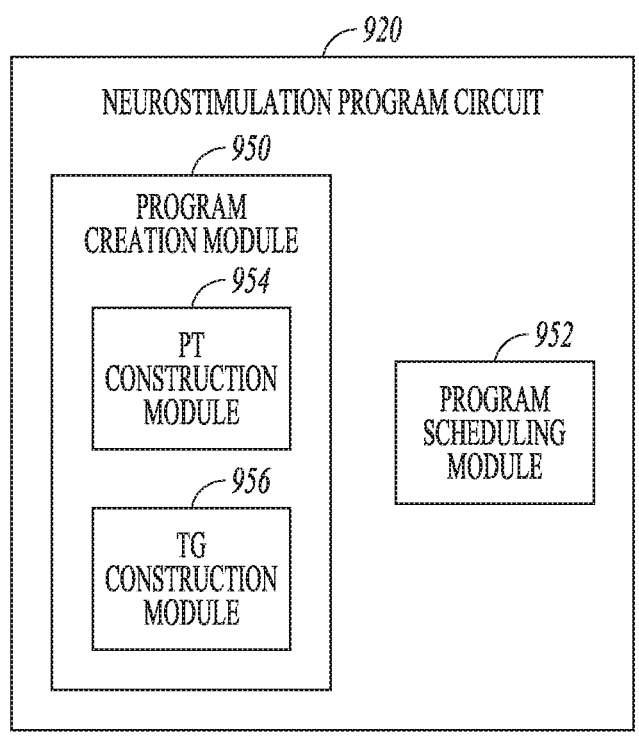
FIG. 9 illustrates an embodiment of a neurostimulation program circuit of an external programming device, such as the external programming device of FIG. 6.

FIG. 9 illustrates an embodiment of a neurostimulation program circuit 920 of an external programming device, such as the external programming device 602. Neurostimulation program circuit 920 is an embodiment of neurostimulation program circuit 320 and includes a program creation module 950 and a program scheduling module 952. In various embodiments, neurostimulation program circuit 920 displays a neurostimulation program area on a display screen, such as display screen 642, in response to a neurostimulation programming command. For example, a user may initiate a programming session for an implantable stimulator by clicking on an icon to open a neurostimulation program window such as illustrated in FIGS. 7 and 8. The neurostimulation program area or window includes the program creation tab and the program scheduling tab such as illustrated in FIGS. 7 and 8. Neurostimulation program circuit 920 receives the program creation command when the program creation tab is selected (e.g., clicked on) by the user, and receives the program scheduling command when the program scheduling tab is selected (e.g., clicked on) by the user.

In response to the program creation command, program creation module 950 displays a PT construction area and TG construction area on the display screen. In the embodiment as illustrated in FIG. 7, the PT and TG construction areas are displayed simultaneously.

PT construction module 954 allows construction of one or more PTs using the PT construction area. In various embodiments, PT construction module 954 allows for (1) adding a PB to a PT and subtracting a PB from the PT, with the PT construction area dynamically updated to reflect the change; (2) cycling through and/or defining different PTs; (3) assigning leads and electrodes (stimulation field) and pulse shape to each PT; (4) specifying cathode(s) and anode(s), such as by clicking on a PB symbol displayed as illustrated in GIG. 7; and (5) loading a PT from the PT library, and saving a newly created PT in the PT library.

TG construction module 965 allows construction of one or more TGs using the TG scheduling area. In various embodiments, TG construction module 954 allows for (1) cycling through and/or defining different TGs; (2) adding one or more PTs and/or stimulation pauses (SPs) to the TG; (3) modify the order of the PTs and/or SPs in the TG, such as by clicking and dragging; (4) PTs and SPs snap to circle; (5) randomization of the order of PBs within a PT; and (6) loading a TG from the TG library, and saving a newly created TG in the TG library.

In response to the programming scheduling command, program scheduling module 952 displays the program scheduling area on the display screen. In various embodiments, TG construction module 954 allows for (1) specification of at least a starting time for each TG in a neurostimulation program; (2) allow multiple programs to be selected to be delivered simultaneously: and loading a program from the program library, and saving a newly scheduled program in the program library.

Figure 10:
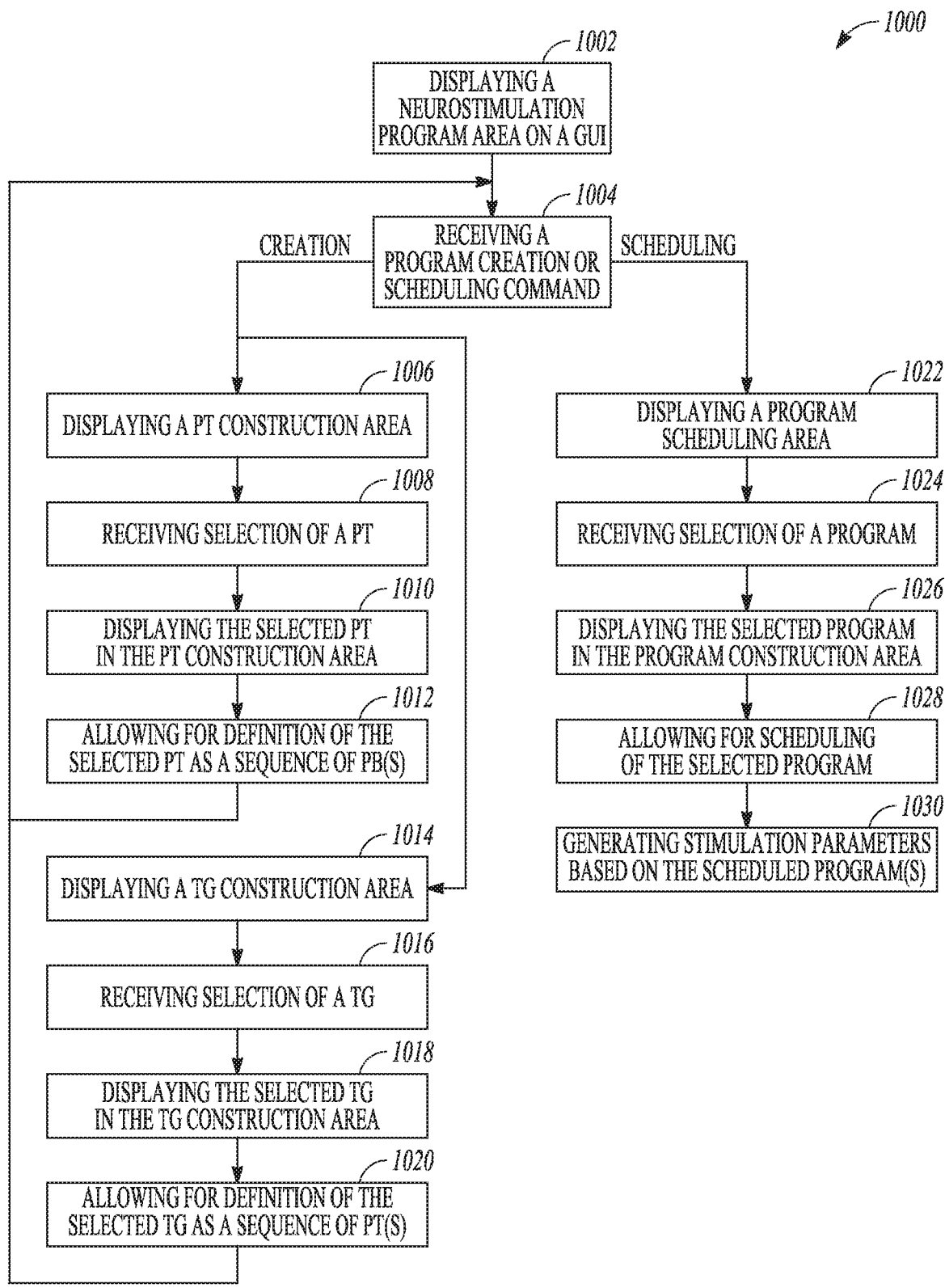
FIG. 10 illustrates an embodiment of a method for creating and scheduling neurostimulation programs.

FIG. 10 illustrates an embodiment of a method 1000 for creating and scheduling neurostimulation programs. In one embodiment, method 1000 is performed using system 100, including the various embodiments of its components as discussed in this document. For example, GUI 610 and neurostimulation program circuit 320 or 920 may be configured for performing method 1000.

At 1002, a neurostimulation program area is displayed on a GUI. The neurostimulation program area allows a user such as a physician or other caregiver to create building blocks for one or more neurostimulation programs and to schedule delivery of the one or more programs. The programs each specify a pattern of the neurostimulation pulses. The one or more building blocks includes one or more PBs each including a plurality of pulses of the neurostimulation pulses, one or more PTs each including one or more PBs, and one or more TGs each including one or more PTs, as discussed above with reference to FIGS. 7 and 8.

At 1004, a program creation command or a program scheduling command is received from the user using the GUI. In response to a program creation command being received at 1004, a PT construction area is displayed at 1006, selection of a PT from the one or more PTs is received from the user at 1008, the selected PT is displayed in the PT construction area at 1010, and definition of the selected PT as a sequence of PB(s) is allowed to be performed by the user. Also in response to the program creation command being received at 1004, a TG construction area is displayed at 1014, selection of a TG from the one or more TGs is received from the user at 1016, the selected TG is displayed in the TG construction area at 1018, and definition of the selected TG as a sequence of PT(s) is allowed to be performed by the user. In various embodiments, when defining a TG, the user is allowed to specify the number of repetitions for the one or more PBs of each PT in the TG. In various embodiments, when defining the TG, the user is also allowed to specify an order (including a random order) of the one or more PBs of each PT in the TG.

In response to a program scheduling command being received at 1004, a program scheduling area is displayed at 1022, selection of a program from the one or more programs is received from the user at 1024, the selected program is displayed in the program scheduling area at 1026, and scheduling of the selected program is allowed to be performed by the user at 1028. In various embodiments, scheduling a program includes specifying time of delivery for each TG in the program. In various embodiments, the user is also allowed to specify a frequency of delivery of the program. In various embodiments, the user is allowed to select multiple programs to be run simultaneously.

At 1030, stimulation parameters are generated based on the scheduled program(s). In various embodiments, the stimulation parameters are transmitted to an implantable medical device, such as implantable stimulator 404, and used to control delivery of neurostimulation pulses from the implantable medical device.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A neurostimulation system, comprising:
    a stimulation device configured to deliver neurostimulation pulses and to control the delivery of the neurostimulation pulses using a plurality of stimulation parameters;
    a storage device configured to store scheduled one or more neurostimulation programs;
    a programming control circuit configured to generate the plurality of stimulation parameters according to the scheduled one or more neurostimulation programs each specifying a pattern of the neurostimulation pulses; and
    a user interface coupled to the programming control circuit and including a display screen, a user input, and a neurostimulation program circuit configured to display a program creation area on the display screen, to create building blocks of the one or more neurostimulation programs, to display a program scheduling area on the display screen, to schedule the one or more neurostimulation programs, and to store the scheduled one or more neurostimulation programs in the storage device, wherein:
        the creation of the building blocks includes construction of pulse trains (PTs) each by temporally arranging one or more pulse blocks (PBs) in the program creation area using the user input device and construction of train groupings (TGs) each by temporally arranging one or more PTs selected from the constructed PTs in the program creation area using the user input device, the construction of each TG of the TGs including specifying an order and a number of repetitions of the one or more PBs in each PT of the selected one or more PTs in that TG, the one or more PBs each including a plurality of pulses of the neurostimulation pulses; and
        the scheduling of the one or more neurostimulation programs includes temporally arranging one or more TGs selected from the constructed TGs for each program of the one or more neurostimulation programs in the program scheduling area using the user input device and specifying one or more delivery times for the each program in the program scheduling area using the user input device.

2. The system of claim 1, wherein the programming control circuit is configured to receive a selection from a plurality of orders for the order of the repetitions of the one or more PBs in each PT of the selected one or more PTs, the plurality of orders including a randomized order and one or more additional orders.

3. The system of claim 2, wherein the programming control circuit is configured to receive the selection from the randomized order and a predetermine order.

4. The system of claim 3, wherein the programming control circuit is configured to receive the selection using the user input device.

5. The system of claim 4, wherein the display screen comprises a touchscreen, and a portion of the user input device is integrated into the touchscreen.

6. The system of claim 1, wherein the one or more neurostimulation programs comprise a plurality of programs, and the neurostimulation program circuit is configured to allow scheduling of the plurality of programs to be delivered simultaneously.

7. The system of claim 1, wherein the storage device includes:
    a PT library having one or more stored Pts;
    a TG library having one or more stored TGs; and
    a program library having one or more stored scheduled programs including the scheduled one or more neurostimulation programs, and wherein the neurostimulation program circuit is configured to:
        allow each of the one or more stored PTs to be used in the construction of a new PT;
        allow the new PT to be added to the one or more stored PTs in the PT library;
        allow each of the one or more stored TGs to be used in the construction of a new TG;
        allow the new TG to be added to the one or more stored TGs in the TG library;
        allow for scheduling of a new program by rescheduling a scheduled program of the one or more stored scheduled programs; and
        allow the new scheduled program to be added to the one or more stored scheduled programs in the program library.

8. A method for neurostimulation, the method comprising:
    receiving information using a user interface including a display screen and a user input device;
    displaying a program creation area on the display screen;
    creating building blocks of one or more neurostimulation programs based on the received information, including constructing pulse trains (PTs) each by temporally arranging one or more pulse blocks (PBs) in the program creation area using the user input device and constructing train groupings (TGs) each by temporally arranging one or more PTs selected from the constructed PTs in the program creation area using the user input device, the construction of each TG of the TGs including specifying an order and a number of repetitions of the one or more PBs in each PT of the selected one or more PTs in that TG, the one or more neurostimulation programs each specifying a pattern of neurostimulation pulses, the one or more PBs each including a plurality of pulses of the neurostimulation pulses;
    displaying a program scheduling area on the display screen;
    scheduling the one or more neurostimulation programs based on the received information, including temporally arranging one or more TGs selected from the constructed TGs for each program of the one or more neurostimulation programs in the program scheduling area using the user input device and specifying one or more delivery times for the each program in the program scheduling area using the user input device;
    generating stimulation parameters according to the scheduled one or more neurostimulation programs;
    delivering the neurostimulation pulses; and
    controlling the delivery of the neurostimulation pulses using the stimulation parameters.

9. The method of claim 8, wherein specifying the order of the repetitions of the one or more PBs in each PT of the selected one or more PTs comprises specifying a randomized order.

10. The method of claim 8, wherein receiving the information comprises receiving the order of the repetitions of the one or more PBs in each PT of the selected one or more PTs.

11. The method of claim 10, wherein receiving the order of the repetitions of the one or more PBs in each PT of the selected one or more PTs comprises receiving a selection from a plurality of orders for the order of the repetitions of the one or more PBs in each PT of the selected one or more PTs using the user input device, the plurality of orders including a randomized order and one or more additional orders.

12. The method of claim 11, wherein the plurality of orders comprises the randomized order and a predetermine order.

13. The method of claim 8, further comprising storing one or more PTs in a PT library of a storage device, and constructing the PTs comprises constructing a new PT using one of the stored one or more PTs in the PT library.

14. The method of claim 13, further comprising storing one or more TGs in a TG library of the storage device, and constructing the TGs comprises constructing a new TG using one of the stored one or more TGs in the TG library.

15. The method of claim 14, further comprising storing one or more scheduled programs including the scheduled one or more neurostimulation programs in a program library of the storage device, and scheduling the one or more neurostimulation programs comprises scheduling a new program by rescheduling a scheduled program of the stored one or more scheduled programs in the program library.

16. A non-transitory machine-readable medium including instructions, which when executed by a machine, cause the machine to perform a method for neurostimulation, the method comprising:
  receiving information using a user interface including a display screen and a user input device;
  displaying a program creation area on the display screen;
  creating building blocks of one or more neurostimulation programs based on the received information, including constructing pulse trains (PTs) each by temporally arranging one or more pulse blocks (PBs) in the program creation area using the user input device and constructing train groupings (TGs) each by temporally arranging one or more PTs selected from the constructed PTs in the program creation area using the user input device, the construction of each TG of the TGs including specifying an order and a number of repetitions of the one or more PBs in each PT of the selected one or more PTs in that TG, the one or more neurostimulation programs each specifying a pattern of neurostimulation pulses, the one or more PBs each including a plurality of pulses of the neurostimulation pulses;
  displaying a program scheduling area on the display screen;
  scheduling the one or more neurostimulation programs based on the received information, including temporally arranging one or more TGs selected from the constructed TGs for each program of the one or more neurostimulation programs in the program scheduling area using the user input device and specifying one or more delivery times for the each program in the program scheduling area using the user input device;
  generating stimulation parameters according to the scheduled one or more neurostimulation programs;
  delivering the neurostimulation pulses; and
  controlling the delivery of the neurostimulation pulses using the stimulation parameters.

17. The non-transitory machine-readable medium of claim 16, wherein specifying the order of the repetitions of the one or more PBs in each PT of the selected one or more PTs comprises specifying a randomized order.

18. The non-transitory machine-readable medium of claim 16, wherein specifying the order of the repetitions of the one or more PBs in each PT of the selected one or more PTs comprises receiving a selection from a randomized order and a predetermine order.

19. The non-transitory machine-readable medium of claim 16, wherein the method further comprises:
  storing one or more PTs in a PT library of a storage device; and
  storing one or more TGs in a TG library of the storage device, and wherein:
    constructing the PTs comprises constructing a new PT using one of the stored one or more PTs in the PT library; and
    constructing the TGs comprises constructing a new TG using one of the stored one or more TGs in the TG library.

20. The non-transitory machine-readable medium of claim 19, wherein the method further comprises storing one or more scheduled programs including the scheduled one or more neurostimulation programs in a program library of the storage device, and scheduling the one or more neurostimulation programs comprises scheduling a new program by rescheduling a scheduled program of the stored one or more scheduled programs in the program library.

* * * * *